(12) United States Patent
Brockway (10) Patent No.: US 7,520,850 B2
(45) Date of Patent: Apr. 21, 2009

(54) FEEDBACK CONTROL AND VENTRICULAR ASSIST DEVICES

(75) Inventor: Brian P. Brockway, Shoreview, MN (US)

(73) Assignee: Transoma Medical, Inc., St. Paul, MN (US)

( * ) Notice: Subject to any disclaimer, the term of this patent is extended or adjusted under 35 U.S.C. 154(b) by 508 days.

(21) Appl. No.: 10/993,826

(22) Filed: Nov. 19, 2004

(65) Prior Publication Data

US 2005/0107658 A1 May 19, 2005

Related U.S. Application Data

(60) Provisional application No. 60/523,408, filed on Nov. 19, 2003.

(51) Int. Cl.
*A61M 1/10* (2006.01)
(52) U.S. Cl. .................................................. 600/17
(58) Field of Classification Search ............... 600/509, 600/513, 16, 17; 607/16, 17; 623/3.1
See application file for complete search history.

(56) References Cited

U.S. PATENT DOCUMENTS

| | | |
|---|---|---|
| 5,588,812 A | 12/1996 | Taylor et al. |
| 5,888,242 A | 3/1999 | Antaki et al. |
| 6,171,253 B1 | 1/2001 | Bullister et al. |
| 6,367,333 B1 | 4/2002 | Bullister et al. |
| 6,481,292 B1 | 11/2002 | Reich |
| 6,540,699 B1 | 4/2003 | Smith |
| 6,949,066 B2 * | 9/2005 | Bearnson et al. ............ 600/16 |
| 2003/0045772 A1 | 3/2003 | Reich et al. |

OTHER PUBLICATIONS

Bullister et al., "Physiologic Control Algorithms for Rotary Blood Pumps Using Pressure Sensor Input," *Artificial Organs*, 26(11):931-938 (2002).
Olsen, D. B., "Presidential Address, The History of Continuous-Flow Blood Pumps," *Artificial Organs*, 24(6):401-404 (2000).

* cited by examiner

*Primary Examiner*—Carl H Layno
*Assistant Examiner*—Frances P Oropeza
(74) *Attorney, Agent, or Firm*—Fish & Richardson P.C.

(57) ABSTRACT

Various devices, systems and methods for providing effective, long term and reliable use of pressure feedback in VADs. Exemplary embodiments are described which provide for direct LV pressure measurement, non-invasive calibration techniques to detect ventricular collapse and recalibrate the feedback mechanism, improved pressure sensor designs with reduced drift, and barometric pressure correction schemes. These devices and methods may be used alone or in combination with each other, and may also be combined with other feedback mechanisms.

5 Claims, 7 Drawing Sheets

FEEDBACK CONTROL AND VENTRICULAR ASSIST DEVICES

FIELD OF THE INVENTION

The present invention generally relates to implantable ventricular assist devices (VADs) and methods of use thereof.

BACKGROUND OF THE INVENTION

Generally, VADs are blood pumps which help the heart pump blood. In certain situations, a patient's heart may need help pumping blood on a short term basis to help the patient recover from a cardiac event or to act as a bridge to heart transplant surgery, or on a long term basis to provide permanent support to the heart. There are several different types of VADs, the most common of which is a left ventricular assist device (LVAD) which helps the left ventricle (LV) of the heart pump oxygenated blood received from the lungs to the rest of the body.

LVADs generally include a pump with an inflow tube connected to the LV of the heart and an outflow tube connected to the aorta. The pump may be a pulsatile flow pump or a continuous flow pump, the latter of which has the advantage of being relatively smaller in size, requires less power, involves fewer moving parts, and is believed to provide some level of auto-control of inflow and outflow pressures.

One type of a continuous flow LVAD is an axial flow pump (AFP) which may use a magnetically suspended rotary impeller (rotor) that is coaxially aligned with the attached ends of the inflow tube and the outflow tube. For example, Thoratec (Pleasanton, Calif.) has developed an AFP type LVAD available under the trade name HeartMate® II. A detailed description of an AFP device is described in U.S. Pat. No. 5,588,812 to Taylor et al.

In operation of such a device, the rotational velocity of the rotor must be sufficient to produce enough blood flow to deliver essential substances to the vital issues and remove products of metabolism, as well as cool the bearings (if used) of the pump and prevent thrombus formation in the pump. However, the rotational velocity of the rotor must not be too high, otherwise a zero or negative pressure may be developed within the left ventricle during diastole, thereby potentially causing ventricular collapse. On occasion if this happens, the LV will collapse momentarily, then refill and collapse again after the LV fills with blood. This oscillatory behavior may be clinically detrimental. Thus, the rotational velocity of the rotor is adjusted to a level that draws the pressure of the LV down to near zero, but not so high as to draw the pressure within the LV to a level at or below zero.

One approach to address this issue is to utilize current from the rotor motor as a feedback mechanism to prevent ventricular collapse. Such an approach is described in U.S. Pat. No. 5,888,242 to Antaki et al. However, it has been shown clinically that using motor current feedback as the only means to prevent ventricular collapse is not always reliable.

Another approach is to provide a pressure transducer in the inflow region of the LVAD and use pressure measurements as a feedback mechanism to infer ventricular collapse. Examples of LVADs incorporating pressure transducers in the inflow tube are described in U.S. Pat. Nos. 6,171,253 and 6,367,333 to Bullister et al., and U.S. Pat. No. 6,481,292 to Reich. However, using inflow pressure to infer collapse is susceptible to error if inflow pressure varies relative to ventricular pressure. In addition, long term use of a conventional pressure sensor is susceptible to pressure drift and attenuation leading to measurement inaccuracies and potentially misleading information transmitted to the LVAD controller, which could lead to either inadequate perfusion (rotational velocity too slow) or ventricular collapse (rotational velocity too fast).

Use of an implanted pressure sensor for feedback is also susceptible to external pressure changes (i.e., changes in barometric pressure). Barometric pressure can change significantly when a weather front moves through the area where the patient resides, when the patient is riding up an elevator in a tall building or traveling in mountainous areas where changes in elevation are frequent and significant. These barometric pressure changes may lead to inaccurate measurements by the implanted pressure transducer, leading to inaccurate feedback data and improper LVAD operation.

Yet another approach is to utilize a sonomicrometer arrangement in combination with a LVAD as described in U.S. Pat. No. 6,540,699 to Smith. A sonomicrometer arrangement utilizes ultrasonic transducers which are allegedly less susceptible to drift than conventional pressure transducers, and therefore may provide a more reliable indication of ventricular collapse. However, in order to obtain an accurate and complete assessment of ventricular collapse, a plurality of ultrasonic transducers should be implanted around the LV. Implanting a plurality of transducers around the heart may be procedurally difficult, and relying on a plurality of transducers increases the likelihood of device failure.

Thus, there is an unmet need for a simple, effective and reliable method of controlling a VAD by drawing the pressure of the LV down to near zero while preventing ventricular collapse.

SUMMARY OF THE INVENTION

To address this need, various embodiments are described herein for providing more reliable and/or accurate pressure feedback. These embodiments, which are described by way of example, not limitation, permit the effective, long term and reliable use of pressure feedback in VADs.

These exemplary embodiments generally improve the efficacy of using pressure feedback by: (1) providing devices and methods for directly measuring LV pressure; (2) providing non-invasive calibration techniques to recalibrate the feedback mechanism; (3) providing improved pressure sensor designs with reduced drift; and (4) providing barometric pressure correction schemes. These devices and methods may be used alone or in combination with each other, and may also be combined with other feedback mechanisms such as motor current.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

The drawings and corresponding text describe various devices, systems and methods for providing more effective, long term and reliable use of pressure feedback in VADs. For example, with reference to FIG. 2, an endocardial pressure sensor is described that may be implanted in or on the heart to directly measure LV pressure and detect ventricular collapse, for the purpose of preventing ventricular collapse and for diagnostic purposes. With reference to FIG. 3, a calibration technique that permits the feedback mechanism of the VAD to be periodically recalibrated in a simple and non-invasive manner addresses the problem of sensor drift. With reference to FIGS. 4-7, a pressure transducer with improved long-term stability is described to address the problem of sensor drift.

The following description is made with reference to an AFP type LVAD for purposes of illustration only. The embodiments described herein may be applied to a variety of cardiac circulatory support devices, including both pulsatile flow and continuous flow types of right ventricular assist devices (RVADs), left ventricular assist devices (LVADs), biventricular ventricular assist devices (BVADs), and total heart pumps (i.e., artificial hearts), for example.

System Level Description

Figure 1:
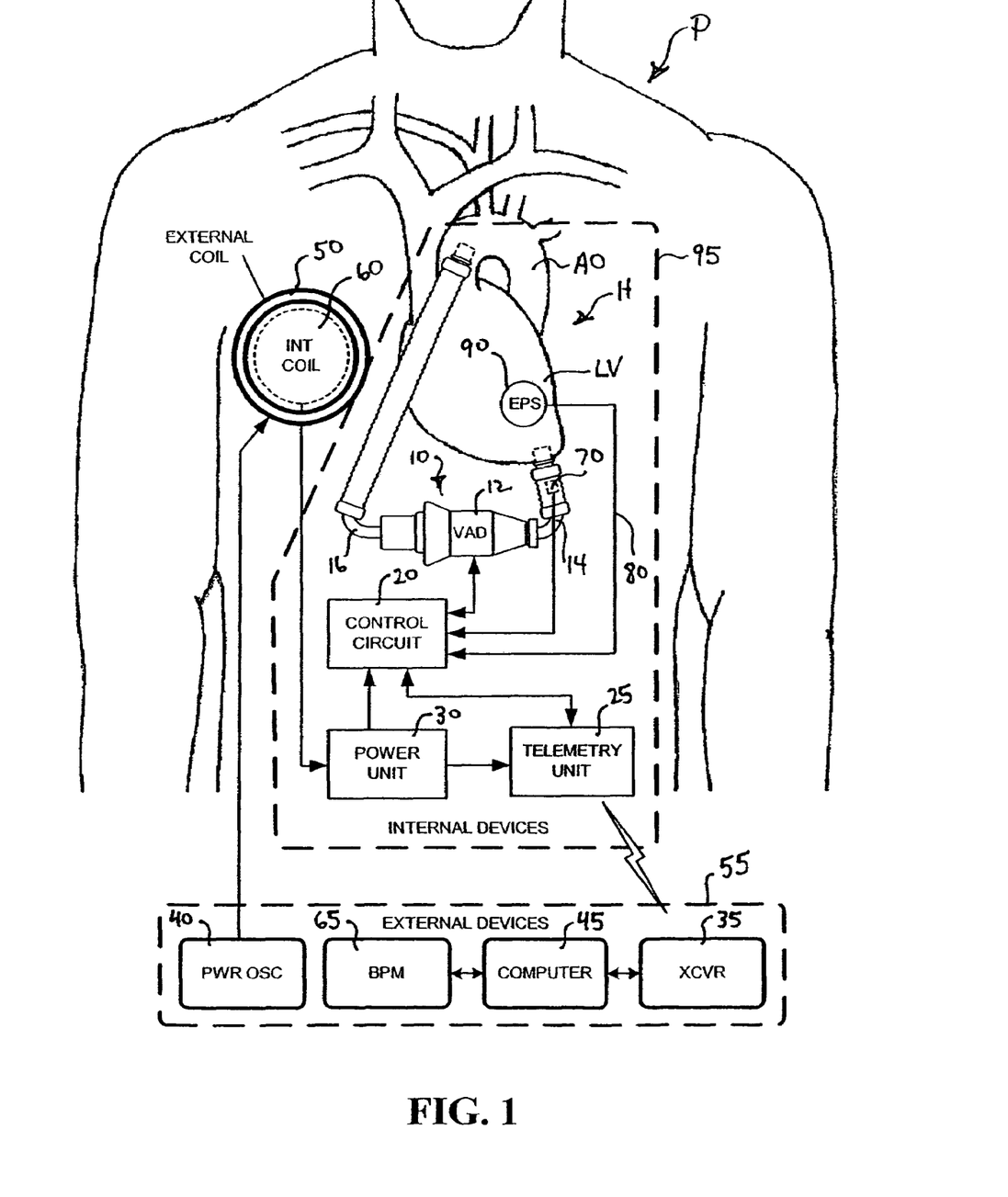
FIG. 1 is a schematic plan view of a LVAD system in accordance with an exemplary embodiment of the present invention.

With reference to FIG. 1, a LVAD system is shown schematically. Except as shown and described; the LVAD system illustrated is similar to the AFP type LVAD available under the trade name HeartMate® II from Thoratec, Inc. (Pleasanton, Calif.). The LVAD system a plurality of internal devices 95, including an AFP type LVAD 10, a control circuit 20 connected to the LVAD. 10 via a bidirectional link (e.g., wire cable), and a power source/storage unit 30 (e.g., rechargeable battery) connected to the control circuit 20. For long term use, the LVAD 10, control circuit 20 and power unit 30 may be configured for chronic implantation. To facilitate such long term use, the power unit 30 may be recharged by utilizing an external power oscillator 40 to drive an external primary coil 50 which induces current flow in a subcutaneous secondary coil 60 connected to the internal power unit 30.

Optionally, the control circuit 20 may be connected to an implantable telemetry unit 25 via a bidirectional electrical connection (e.g., wire cable), which may be remotely connected to an external receiver or transceiver 35 via a wireless bidirectional link (e.g., RF, microwave, ultrasound, magnetic, etc.). The transceiver 35 may be connected to a programmer or computer 45 to facilitate, for example, operational data download, physiological data download, programming data upload, etc. A barometric pressure monitor (BPM) 65 may be connected to the computer 45 to facilitate barometric pressure correction as will be discussed in more detail hereinafter. The transceiver 35, the computer 45, the power oscillator 40, the primary coil 50, and the BPM 65 may all be external to the patient (P) (i.e., not implanted) and may be collectively referred to as external devices 55. All or some of the external devices 55 may be made sufficiently small to be attached to the patient's belt, worn on the neck as a pendant, on the wrist like a watch, in a garment or elastic band worn about the patient's chest or abdomen, or placed in a purse or briefcase.

The LVAD 10 includes an AFP 12 connected to an inflow tube 14 and an outflow tube 16. When implanted, the inflow tube 14 is connected to the LV of the heart (H), and the outflow tube 16 is connected to the aorta (AO), thus supplementing blood flow from the LV to the arterial system of the rest of the patient's body. The AFP 12 generally includes a rotary impeller (rotor) magnetically suspended in a hollow cylindrical motor stator. Further details of the AFP 12 design may be found in U.S. Pat. No. 5,588,812 to Taylor et al., the disclosure of which is incorporated herein by reference. The rotor of the AFP 12 is electrically driven inside the stator at a rotational velocity sufficiently high to pump blood from the LV to the AO to satisfy the circulatory requirements of the body, and sufficiently low to avoid collapse of the LV.

Description of Direct LV Pressure Measurement Technique

The use of motor current as a feedback mechanism to control pump output and avoid ventricular collapse has been previously proposed, but may not be clinically reliable. The use of an inlet pressure sensor (IPS) 70 as a feedback mechanism to infer ventricular collapse has also been previously proposed, but may be susceptible to error if inflow pressure varies relative to ventricular pressure. Typically, the IPS 70 is disposed in the inflow tube 14 of the LVAD 10.

To avoid the potential inaccuracies and/or discrepancies involved in using motor current feedback or inlet pressure feedback to infer ventricular collapse, an endocardial pressure sensor (EPS) 90 may be disposed on the LV free wall adjacent the inlet port to directly measure LV pressure. Thus, to the extent that motor current or inflow pressure is not a reliable predictor of ventricular collapse, the EPS 90 may be used to measure LV pressure as a surrogate for or as a supplement to motor current measurement or inlet pressure measurement.

Figure 2:
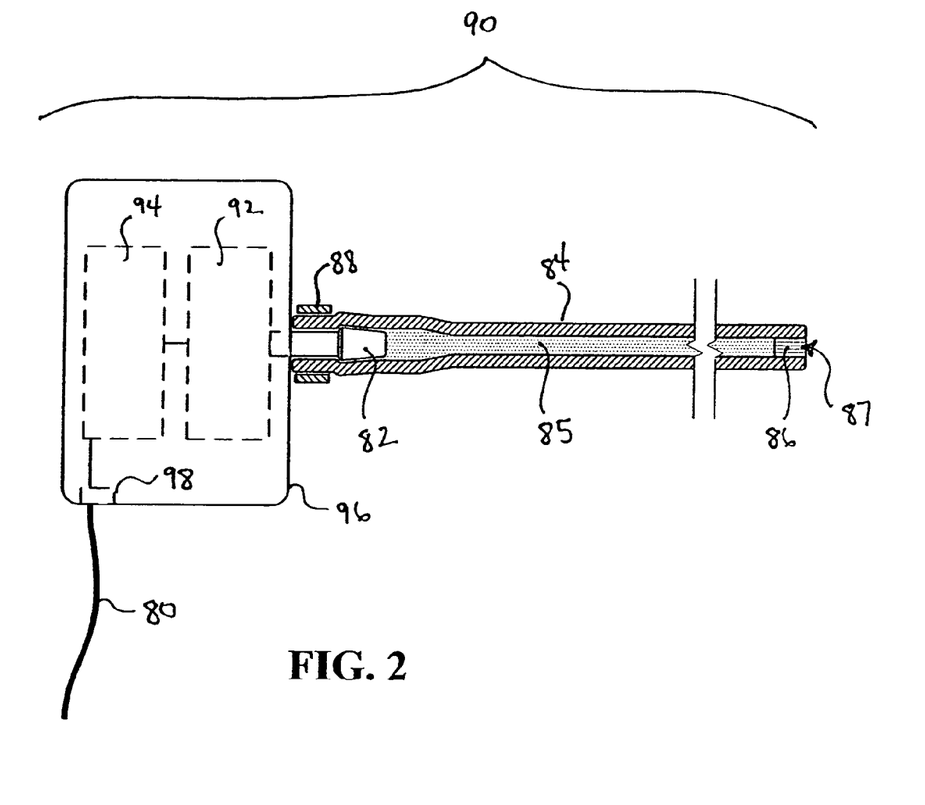
FIG. 2 is a schematic illustration of an endocardial pressure sensor for use with the LVAD shown in FIG. 1 according to an exemplary embodiment of the present invention.
Figure 3:
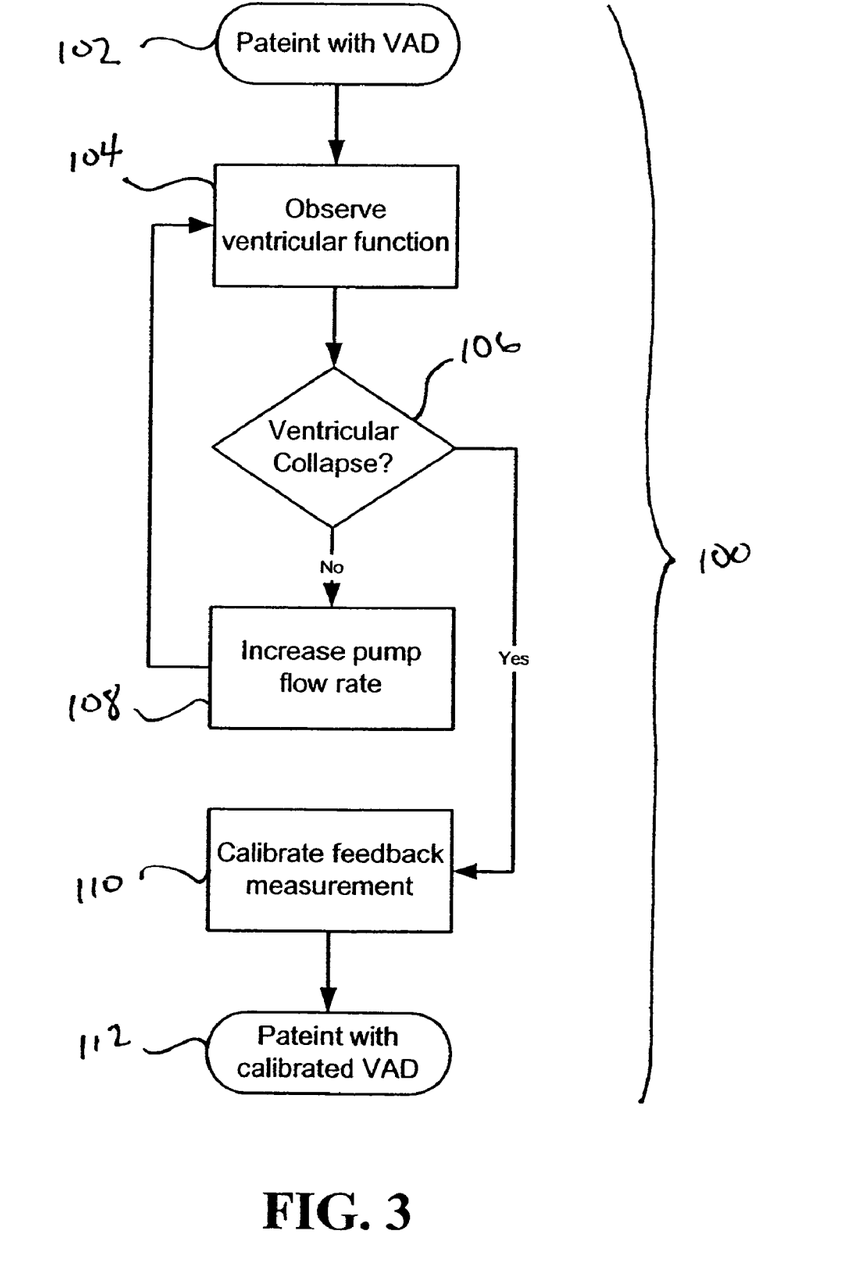
FIG. 3 is a flow chart illustrating a calibration method in accordance with an exemplary embodiment of the present invention.

A detailed description of a suitable EPS 90 is provided with reference to FIG. 2. The EPS 90 may be used to measure LV pressure which may be used to control motor speed of the AFP 12 to maximize flow rate and minimize ventricular collapse. For example, the EPS 90 may be connected to the control circuit 20 to provide pressure feedback thereto for closed-loop control of the LVAD 10. Optionally, the control circuit 20 may telemeter pressure data via telemetry unit 25 and transceiver 35 for open-loop control of the LVAD 10 by the patient or physician, utilizing computer 45, for example. LV pressure obtained by EPS 90 may be used alone or in combination with other feedback mechanisms such as motor current feedback or inflow pressure feedback to control the LVAD 10.

Description of Endocardial Pressure Sensor

With reference to FIG. 2, an example of a suitable EPS 90 is schematically illustrated. Generally, the endocardial pressure sensor 90 may be implanted in or on the heart to directly measure LV pressure and derive LV volume. The EPS 90 includes a pressure transducer 92 and an electronics module 94 contained within a hermetically sealed titanium housing 96. The pressure transducer 92 may be a piezoresistive type transducer as described with reference to FIGS. 4-7.

The electronics module 94 may provide excitation to the pressure transducer 92, amplify the pressure signal, and digitally code the pressure data for communication with the control circuit 20 or the telemetry unit 25 to relay pressure data to the external transceiver. A temperature measurement device may be included within the electronics module 94 to compensate the pressure signal from temperature variations. Other aspects of the EPS 90 may be the same or similar to those described in U.S. Patent Application Publication No.

2002/0120200 to Brockway et al., the entire disclosure of which is incorporated herein by reference.

The proximal end of the housing 96 includes an electrical feedthrough 98 to facilitate connection of the electronics module 94 to a flexible lead 80, which may be connected to the control circuit 20 as shown in FIG. 1. The distal bottom side of the housing 96 includes a pressure transducer header to facilitate mounting of the pressure transducer 92 and to facilitate connection to a pressure transmission catheter (PTC) 84. The housing 96 may be configured for attachment to the heart wall by incorporating anchors, suture ties, etc. The housing 96 may be fabricated of a material (e.g., ceramic) to allow telemetric transmission from one or more antennae inside the housing 96 and/or may be formed of a metallic material and include one or more antennae outside the housing 96 to allow for wireless transmission of the measured pressure signal directly to the transceiver 35 which may then transmit a signal (corrected for barometric pressure variation) back to the controller 20.

The PTC 84 refers pressure from the pressure measurement site (e.g., LV) to the pressure transducer 92 located inside the housing 96. The PTC 84 may comprise a tubular structure with a liquid-filled lumen 85 extending therethrough to a distal opening 87 or port. The PTC 84 may comprise a wide variety of materials, constructions and dimensions depending on the particular characteristics of the bodily tissue in which the PTC 84 resides when implanted. Various materials and construction alternatives for the PTC 84 are described in U.S. Provisional Patent Application No. 60/454,823, filed Mar. 12, 2003, and entitled PRESSURE TRANSMISSION CATHETER FOR IMPLANTABLE PRESSURE SENSORS, the entire disclosure of which is incorporated herein by reference.

The proximal end of the PTC 84 is connected to the pressure transducer via a nipple tube 82, thus establishing a fluid path from the pressure transducer 92 to the distal end of the PTC 84. The proximal end of the PTC 84 may include an interlocking feature to secure the PTC 84 to the nipple tube 82. For example, the nipple tube 82 may have an enlarged head as shown, and a compression band 88 may be disposed around the proximal end of the PTC 84 to provide compression onto the interlocking feature of the nipple tube 82.

A barrier 86 such as a gel plug and/or membrane may be disposed in or over the distal opening to isolate the liquid-filled lumen of the PTC 84 from bodily fluids and to retain the fluid in the lumen, without impeding pressure transmission therethrough. In one embodiment, the fluid is chosen to be a fluorinated silicone oil and the gel is chosen to be dimethyl silicone gel. Further aspects of suitable fluids and gels are described in U.S. patent application Ser. No. 10/272,489, filed Oct. 15, 2002, entitled IMPROVED BARRIERS AND METHODS FOR PRESSURE MEASUREMENT CATHETERS, the entire disclosure of which is incorporated herein by reference.

By way of example, not limitation, the PTC 84 may have a length of approximately 25 mm, an inside diameter of approximately 0.025 inches, and a distal shaft diameter of approximately 0.055 inches for LV pressure monitoring applications as shown and described with reference to FIG. 1. Various tapers, flares, wall thicknesses, etc. may also be incorporated into the PTC 84 without significant departure from these approximate dimensions.

Description of Calibration Techniques

Regardless of the type of feedback utilized to control the VAD, the feedback mechanism may be susceptible to drift over time. For example, with both the EPS 90 and the IPS 70, a piezoresistive type pressure transducer may be employed, and the zero offset of such transducers is subject to drift at a finite rate over extended periods of time. Thus, it may be desirable to provide for calibration of the feedback mechanism (e.g., LV pressure, inlet pressure, or motor current) for the VAD post implantation.

With reference to FIG. 3, a flow chart illustrating a calibration method 100 is shown for calibration and/or recalibration of the feedback sensor (e.g., EPS 90, IPS 70 or motor current sensor). This exemplary calibration technique 100 permits feedback sensors associated with a VAD to be periodically recalibrated in a simple and non-invasive manner to address the problem of calibration drift. This calibration method is described with primary reference to EPS 90, but may also be applied to other feedback mechanisms and sensors.

Generally, this method 100 involves taking sensor reading(s) (e.g., pressure measured by the EPS 90) while monitoring the motion of the heart wall, preferably by a non-invasive manner. In this exemplary method 100, a patient having an implanted VAD is presented 102 at a hospital, clinic or other medical facility with suitable diagnostic capabilities. This may be done at the time of implantation or subsequent thereto. The ventricular function (e.g., LV function for LVADs) of the patient is observed 104, using a technique such as trans-esophageal echo (TEE), intracardiac echo (ICE), transthoracic echo, or transluminal intraventricular pressure measurement (e.g., with a highly accurate pressure-sensing catheter such as those available from Millar Instruments (Houston, Tex.) placed in the ventricle). Relatively non-invasive ultrasonic techniques such as TEE may be preferred for most patients.

With the VAD running, the ventricle is observed 106 for onset of ventricular collapse 106, as would occur if the intraventricular pressure neared intrathoracic pressure during some portion of the cardiac cycle. If the ventricle is not nearing collapse, the pump flow rate of the VAD is incrementally increased 108 by, for example, increasing the rotational velocity of the AFP, and steps 104 and 106 are repeated. If the ventricle is starting to collapse, the pressure in the ventricle is close to intrathoracic pressure (zero), and represents a critical reference point for control of the VAD. The feedback sensor is calibrated 110 to correspond to near zero (or within the incremental increase of step 108) to establish endocardial pressure (or other feedback parameter) consistent with LV collapse. The feedback sensor may be calibrated by adjusting the sensor output by programming new calibrations into a memory chip associated with the sensor electronics or VAD control circuitry. Alternately, the sensor electronics can be designed to contain a programmable offset value (positive or negative, depending on the sign of the numerical value of the zero offset). Once the zero offset drift has been identified using this procedure, the offset can be programmed into the sensor electronics or VAD control circuitry and the sensor measurement used by VAD control electronics will be adjusted by the newly stored offset value. The feedback sensor is thus calibrated and operation of the VAD is corrected 112 for calibration drift.

It may be beneficial if the parameter (e.g., pressure) measured by the feedback sensor (e.g., EPS 90) could be transmitted out of the patient for observation during this procedure. Further it may be beneficial to perform this same protocol (turn motor speed up manually until the ventricle begins to collapse) shortly after the VAD is implanted, at which time the feedback sensor will still be highly accurate (i.e., has not drifted). This method basically allows feedback sensor measurement at a point which the ventricle begins to collapse, and subsequent procedures may be used to adjust the feedback sensor output to this same value in order to correct for the occurrence of excessive drift.

Description of Pressure Sensors with Improved Stability

In addition or alternative, it may be desirable to provide an improved pressure sensor in the EPS 90 and/or IPS 70 that is more stable over time, as described with reference to FIGS. 4-7. A more detailed description of these and other pressure sensors with reduced drift are described in U.S. patent application Ser. No. 10/717,179, filed Nov. 17, 2003, entitled IMPLANTABLE PRESSURE SENSORS to Zwiers et al, the entire disclosure of which is incorporated herein by reference.

Figure 4:
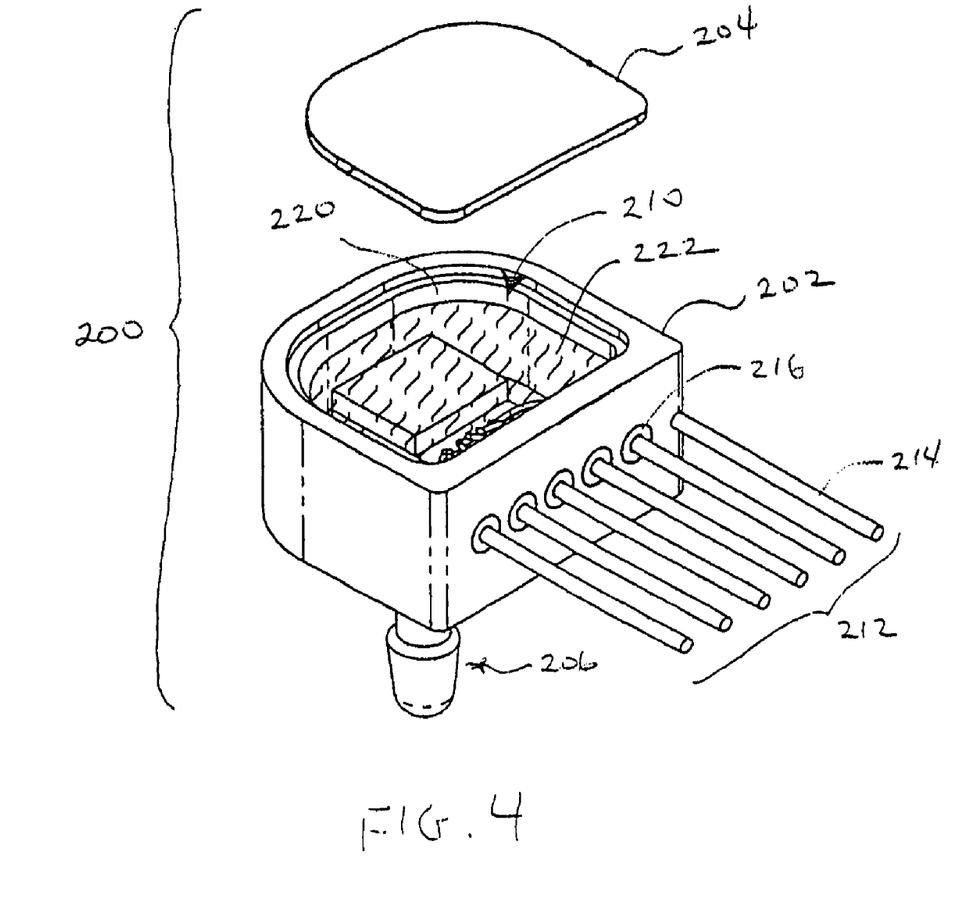
FIGS. 4-7 are illustrations of a pressure transducer with increased stability for use as the inflow pressure sensor or endocardial pressure sensor with the LVAD shown in FIG. 1 according to an exemplary embodiment of the present invention.

With reference to FIGS. 4-7, an improved pressure sensor 200 for use in the EPS 90 and/or IPS 70 is illustrated. The pressure sensor 200 has improved long term stability to address the problem of sensor drift. For purposes of illustration only, the improved pressure sensor 200 is shown as it would be implemented as an EPS 90 (PTC 84 and electronics module 94 not shown), but may be implemented as an IPS 70 by mounting the pressure sensor 200 on the outside of the inflow tube 14 and establishing a fluid path from the interior of the tube 14 to the PTC 84. In FIG. 4, the improved pressure sensor 200 is shown partially exploded to expose the internal components 210. Pressure sensor 200, inclusive of a pressure transmission catheter 84 and electronics module 94 (not shown), may be used in place of EPS 90 described previously. As constructed herein, the pressure sensor 200 may provide an average drift rate of less than 0.75 mmHg per month, preferably less than 0.50 mmHg per month, and more preferably 0.10 mmHg per month or less.

Pressure sensor 200 includes a lower housing unit 202 and a cover plate 204, both of which may be formed of a chronically implantable biocompatible material such as Titanium, and may be hermetically sealed together using conventional techniques. A nipple tube 206 extends from the bottom surface of the lower housing unit 202 for connection to a pressure transmission catheter 34 (not shown) as described previously. Each of a plurality of electrical leads 212 extend through the lower housing unit 202 via insulative hermetically sealed rings 216, with the exception of a ground lead 214 that may be directly connected to the lower housing unit 202.

When assembled, the lower housing unit 202 and the cover plate 204 define an internal cavity 220, in which a plurality of internal components 210 may be disposed and covered (encapsulated) by a suitable encapsulant material 222 such as a fluoro-silicone material that partially fills the internal cavity 220. Internal cavity 220 acts as a means for pressure relief to accommodate pressure variations that may occur over time due to environmental (e.g., temperature) changes, for example. Encapsulant material 222 provides a non-hermetic seal that may permit the egress of water vapor into the internal cavity 220, but serves to protect the otherwise exposed electrical components from corrosion and dendrite growth which may cause electrical shorts. As used herein, hermetic may be defined as a helium leak rate of less than $1 \times 10^{-8}$ cm$^3$/sec at 1.0 ATM. Suitable encapsulant materials include: phenyl, dimethyl, and fluoro silicone gels and soft polymers; hydro gels; and other soft (e.g., <60 Durometer Shore Zero Harness Scale) polymeric materials that are not immiscible in the other materials used (e.g., adhesives) in the cavity 220.

Figure 5:
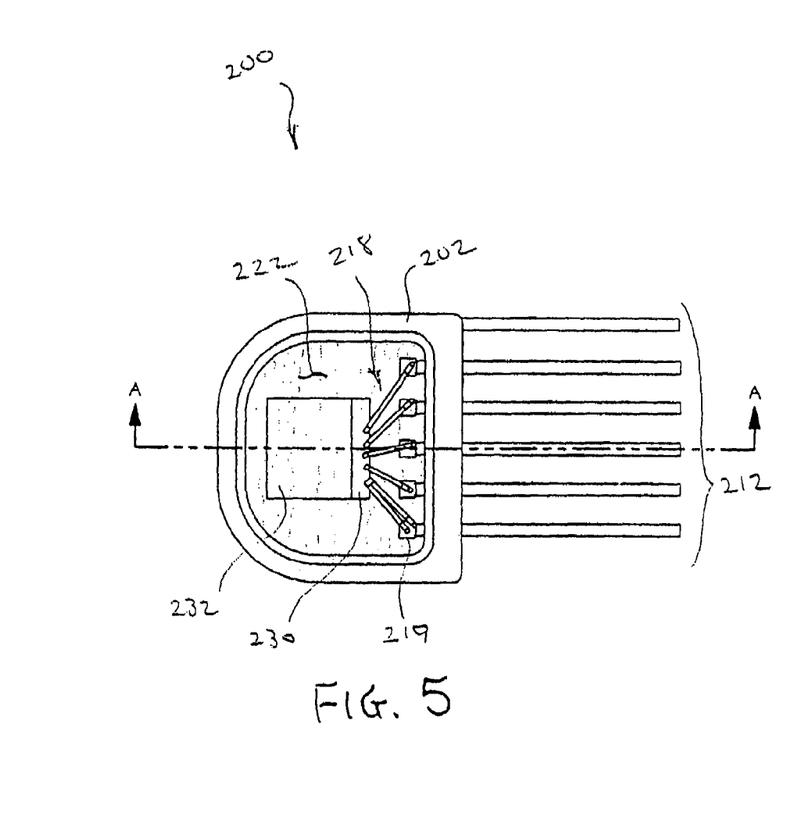

With reference to FIG. 5, a pressure sensing element 230, such as a piezo-resistive Wheatstone bridge type silicon strain gauge available from Sensonor of Horten, Norway, includes a plurality of wires 218 connected to the leads 212 via bonding pads 219. Leads 212 may comprise a platinum-iridium core coated with nickel and aluminum. Wires 218 and bonding pads 219 may comprise aluminum, which tends to be highly corrodible in the presence of water, tends to form dendrites when exposed to a voltage potential in the presence of water vapor and ionic contaminants, tends to be susceptible to electrical shorts in the presence of water, all of which may be commonly encountered in the implanted environment. Because of these issues, encapsulant 222 serves to protect the wires 218 and pads 219 from the adverse effects associated therewith.

Figure 6:
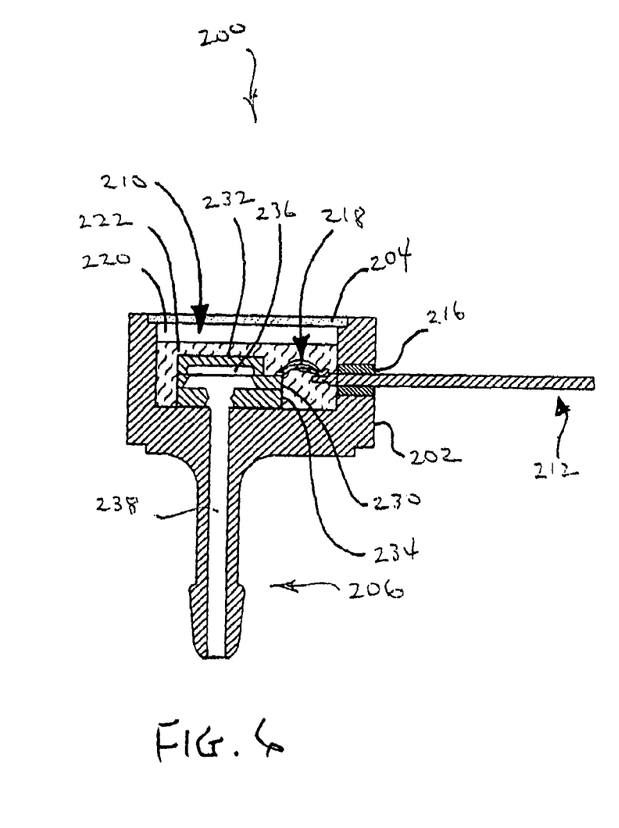

With reference to FIG. 6, which is a cross-sectional view taken along line A-A in FIG. 5 (including top cover), the structure of the internal components 210 may be more readily appreciated. The bottom portion of the sensor element 230 is mounted to a constraint 234 (also referred to as pedestal or stand-off), and a reference cover 232 is mounted to the top portion of the sensor element 230 to define a reference cavity 236 (e.g., vacuum) therebetween. The bottom portion of the constraint 234 is mounted to the lower housing unit 202 in alignment with the nipple tube. A fluid path is defined via lumen 238 that extends from the underside of the sensing element 230 (referred to as backside access), through the constraint 234, through the nipple tube 206, and into the PTC mounted thereto, thus enabling fluidic transmission of pressure signals from the distal end of the PTC to the sensor element 230.

The sensing element 230, reference cover 232, and constraint 234 may be collectively referred to as a sensor die. The housing 202 to which the sensor die is mounted may be referred to as a header. The bond between the sensor dies and the header may be referred to as a die mount. By way of example, not limitation, the sensor element 230 may comprise silicon, and both the constraint 234 and the reference cover 232 may comprise a borosilicate glass (e.g., Pyrex or silica). Also by way of example, the reference cover 232 may be mounted to the sensor element 230 by a glass frit bond, and the sensor element 230 may be mounted to the constraint 234 by an anodic bond, or visa-versa. Further by way of example, the constraint 234 may be mounted to the header by a dymethyl silicone adhesive borid, an epoxy bond, etc.

The die mount may be rigid, referred to as a hard mount, as with a solder joint. Alternatively, the die mount may be flexible, referred to as a soft mount, as with an adhesive joint. A soft mount provides an effective strain relief that isolates the sensor element 230 from header stress, and allows the sensor element 230 to respond only to pressure variations in the lumen 238. For example, because the sensor die and the header comprise different materials with different thermal coefficients of expansion, temperature deviations from the temperature at which the die mount was formed results in a buildup of stress at the die mount. If a hard mount is used, the stress is transferred to the sensor element 230 and is indistinguishable from stresses caused by true pressure changes in the lumen 238. Because the stress may gradually increase and decrease, the resultant pressure measurement error may appear to drift over time. A soft mount minimizes the transfer of stresses to the sensor die from the header due to thermal expansion and contraction. Thus, a soft mount is preferred to minimize the transfer of stress from the header, which improves pressure measurement accuracy. However, an adhesive soft mount does not create a hermetic seal whereas a solder hard mount does create a hermetic seal. Thus, a soft mount that is also hermetic may be desirable is some applications. To address this need, the constraint 234 may comprise a flexible thin metallic structure such as a bellows or an annular flange.

Figure 7:
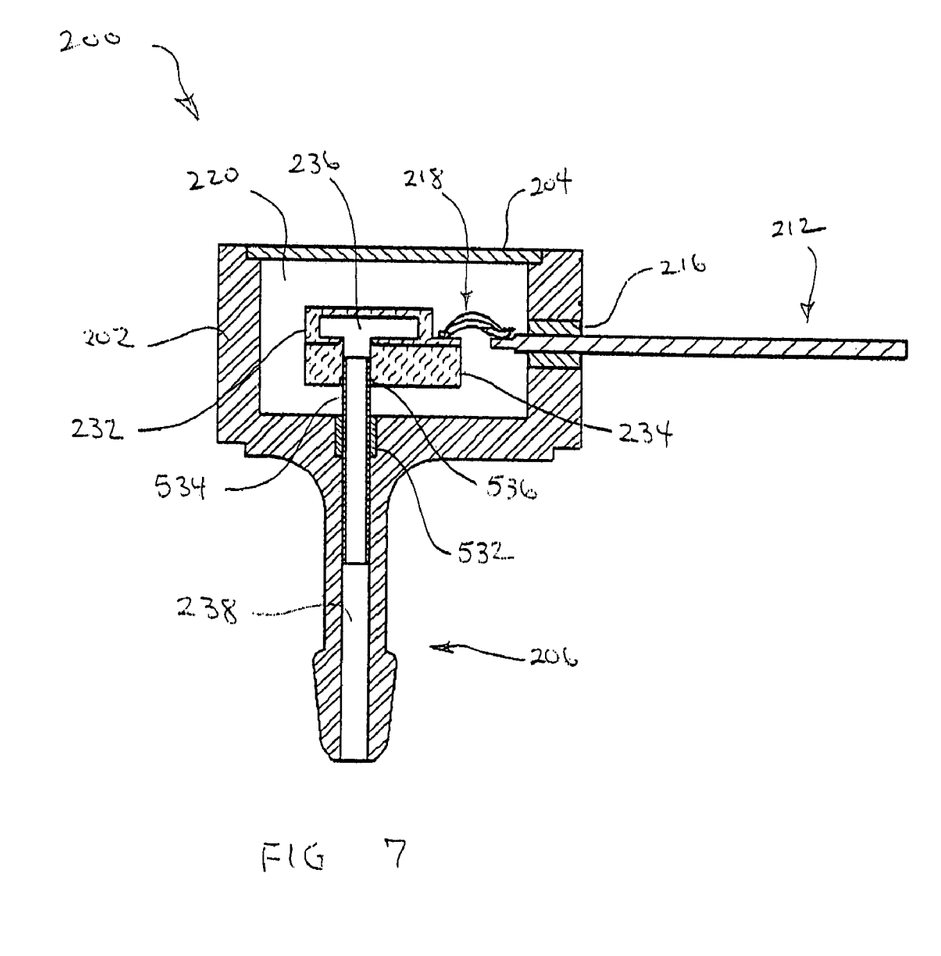

An alternative approach to address the need for a hermetic seal while minimizing mechanically and thermally induced stress is to use an isolation tube 534 as shown in FIG. 7. Tube 534 extends into lumen 238 and provides a lumen in communication with the cavity 236. Tube 534 may comprise borosilicate glass (e.g., Pyrex™ or silica) or a low expansion iron-nickel-cobalt alloy (e.g., Kovar™) and may be hermetically sealed to the housing 202 by joint 532, which may comprise a braze, solder, or glass solder (low melt temperature glass). The housing 202 may comprise a metal (e.g., Ti) which readily accepts a braze, solder or glass solder joint 532. If glass is utilized for tube 534, the outside surface of the glass tube 534 readily accepts a glass solder joint 532 without modification, but may be metalized to facilitate a braze or solder joint 532. Similarly, the tube 534 may be hermetically sealed to the constraint 234 by a joint 536 such as a solder joint facilitated by metalizing the adjacent surfaces of the glass tube 534 and the glass constraint 234. Alternatively, joint 536 may comprise a glass solder joint but care must be taken to avoid thermal damage to the constraint 234 and other components of the sensor.

The tube 534 and the constraint may be formed of the same or similar glass material (e.g., Pyrex or silica) to provide the same or similar coefficient of thermal expansion in order to minimize thermally induced stress therebetween. The tube 534 and the constraint may be also be formed of dissimilar materials (e.g., Kovar and Pyrex) and still provide strain relief effects by virtue of the tube geometry which isolates the constraint from the housing. Generally speaking, the tube 534 acts as a strain relief to isolate the constraint 234 from the housing 202 in order to minimize mechanically and thermally induces stress therebetween, while maintaining a hermetic seal, thereby lowering drift and preventing the migration of water into the interior cavity 220 of the sensor 200.

Optionally, the interior cavity 220 may be filled with an encapsulant as described previously, but the provision of hermetic seals 532 and 536 minimizes or eliminates the need therefor. For example, an encapsulant may be utilized if the seals 532 and 536 are not perfectly hermetic, but provide low permeability to water (e.g., epoxy bonds).

Description of Barometric Pressure Correction Techniques

In each of the foregoing embodiments, and all prior art embodiments that utilize pressure as a feedback parameter, the pressure measurements may be influenced by external pressure changes (i.e., changes in barometric pressure), potentially leading to inaccurate pressure feedback data and improper LVAD operation if not corrected. To address this potential problem, a number of different pressure correction schemes are described herein to address barometric pressure correction of pressure feedback measurements for LVAD operation.

An example of a general approach to barometric pressure correction is to simultaneously take barometric pressure readings with measurements taken by the EPS 90 and/or IPS 70, and subtract the barometric reading from the internal pressure measurement. An example of another general approach is to occasionally take barometric pressure readings, store the reading, and, when needed, subtract the stored value from the measurements taken by the EPS 90 and/or IPS 70.

The subtraction step may be performed by the control circuit 20 or by one of the external devices 55 such as computer 45. If performed by the control circuit 20, the barometric pressure reading is taken by the external device 55 and transmitted to (and optionally stored in) the control circuit 20. If performed by the computer 45, the internal pressure measurement is taken by the EPS 90 and/or IPS 70 and transmitted to the computer 45. The corrected pressure values may then be transmitted to controller 20 via transceiver 35 and telemetry unit 25. It may be preferable to have the control circuit 20 store the barometric reading and perform the subtraction step in order to provide more efficient closed-loop feedback control of the LVAD 10.

In an illustrative embodiment, an external barometric pressure monitor (BPM) 65 measures barometric pressure at specified times. Measurements obtained by the BPM 65 are representative of the barometric pressure to which the body of the patient is exposed. The BPM 65 is powered on, and an initial barometric pressure measurement is taken and stored in memory (e.g., in BPM 65 or computer 45). The barometric pressure measurement is transmitted to the internal control circuit 20, where it is stored in memory. The control circuit 20 is thus able to subtract the stored barometric pressure measurement from the measurements taken from EPS 90 and/or IPS 70. Each subsequent barometric pressure measurement taken by the BPM 65 is compared to the stored measurement and evaluated to determine if the difference between that measurement and the stored measurement exceeds a predetermined threshold (e.g. 0.5 mmHg). If the difference is less than the threshold, no further action is taken on that measurement. If the difference is greater than or equal to the threshold, then that new value is saved in memory and transmitted to the control circuit 20 for use as the updated barometric pressure measurement.

Description of Alternative Barometric (Reference) Sensors

Figure 8A:
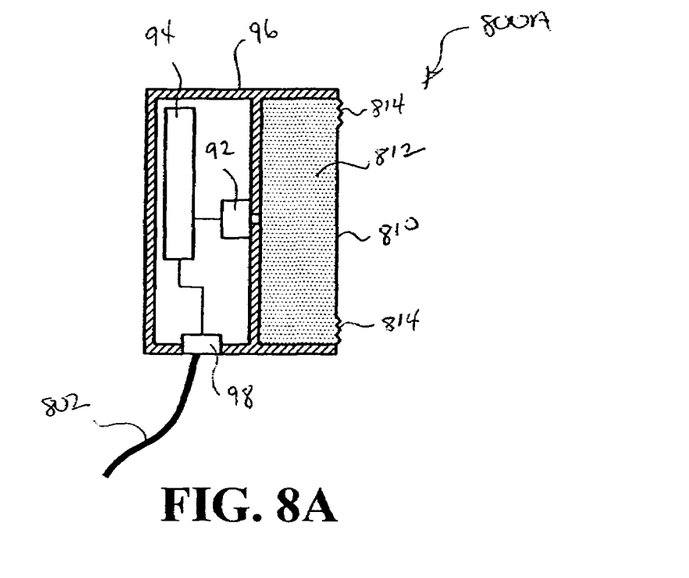
FIGS. 8A and 8B are schematic illustrations of internal reference pressure sensors for use in correcting for variations in barometric pressure.
Figure 8B:
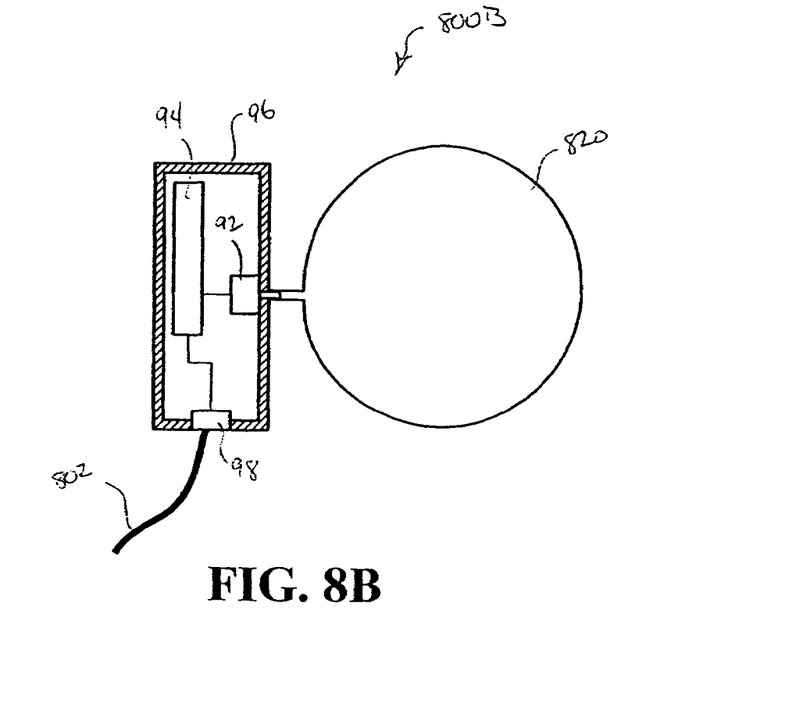

Barometric pressure (or reference pressure) may alternatively be measured through the use of a pressure sensor located within the body. FIGS. 8A and 8B schematically illustrate examples of suitable internal reference pressure sensors 800A, and 800B, respectively. The internal reference pressure sensor 800A or 800B may be implanted inside the body, such as in the thorax.

With reference to FIGS. 8A and 8B, the internal reference pressure sensors 800A/800B each include a housing 96 containing a pressure transducer 92 connected to electronics module 94, which is connected to lead 802 via feedthrough 98, similar to embodiments described previously. The internal barometric pressure sensor 800A/800B may be directly linked to the controller 20 of the VAD 10 via lead 802.

With specific reference to FIG. 8A, the pressure sensor 800A includes a sensing surface 810 which, together with housing 96, defines an internal cavity 812 that may be filled with an oil or other liquid such as a perfluorocarbon, or fluorinated silicone, for example, such as the fill fluid 85 described previously. The sensing surface 810, which may be formed of a metallic membrane for example, functions as a diaphragm to transmit external pressure via the fill fluid to the pressure transducer 92. Because the housing 96 may be relatively rigid, the sensing surface 810 may include bellows 814 or other suspension structure to efficiently deflect in response to pressure variations. The sensing surface 810 may have a relatively large surface area (>20 mm sq) in order to accurately sense pressure following the formation of scar tissue on the sensor surface, as is common if implanted in tissue.

With specific reference to FIG. 8B, the pressure sensor 800B includes a balloon-type sensing surface 820 which may provide relatively more surface area. The balloon-type sensing surface 820, which may be formed of a polymeric material such as urethane for example, may contain a fill fluid as described above and to transmit external pressure via the fill fluid to the pressure transducer 92. The fill fluid may comprise a fluid that has negligible migration through the balloon material, such as the fluids described above. The balloon-type sensing surface 820 may have a relatively large surface area (>20 mm sq) in order to accurately sense pressure following the formation of scar tissue as described previously.

When the reference pressure is measured within the body (e.g., thorax) using an internal pressure sensor such as sensor 800A or 800B, for example, the measurements may be subject to large sudden changes that should be ignored when used for correcting a LV pressure for barometric pressure. Such large sudden changes may be caused by coughing, movements, impacts such as jumping, falling etc. One approach for ignoring or effectively eliminating such large sudden changes is to perform a moving average of the measurements in addition to a median filtering that removes outlier measurements that occur during the events. Another approach is to revert to other feedback control means (e.g., motor current or flow) when a large sudden change in pressure is detected, and return to pressure, feedback control when the barometric (reference) pressure measurements stabilize.

Description of Pressure Corrected Motor Current Feedback

As described above, barometric pressure may be corrected by transmitting pressure from the in vivo sensor to a device worn on the patient or located nearby, substantially as described above. The BPM 65 receives via transceiver 35 and telemetry unit 25 an in-vivo pressure signal (e.g., from EPS 90), corrects for ambient pressure changes, and transmits the corrected signal back to the VAD control circuit 20. The BPM 65 may optionally store pressure data in memory storage device such as computer 45 for later evaluation for use in clinical assessment of the patient, or for evaluation of VAD 10 function.

In some instances, a corrected pressure signal may not always be reliably available. This situation may arise in situations where the patient loses the external device that measures barometric pressure (e.g., BPM 65) or the telemetry link from the external transceiver 35 to the internal telemetry unit 25 is lost or corrupted by electrical noise, or when some event causes a sudden artifact in the barometric pressure signal that is irrelevant to control of the VAD. This is particularly important if the patient is in a situation where ambient pressure is changing rapidly. One such situation is where the patient is riding an elevator from the ground floor of a building to a point several stories above ground level. In such a case, the ambient pressure may change by several mmHg. If the VAD 10 were solely dependent on measured pressure, and one of the foregoing situations were to arise, an inappropriate response in VAD control may take place.

One approach to dealing with this situation is to employ motor current or pump output flow as a primary feedback means, and use pressure (e.g., ventricular pressure as measured by EPS 90) to correct or calibrate motor current on a frequent basis. With this approach, pressure may be used to calibrate motor current only at times when the ventricular pressure is verified as accurate and reliable. This approach has a secondary advantage in that continuous pressure recording is not required, which may allow for power conservation of the internal devices 95.

To determine if ventricular pressure is reliable and accurate, certain evaluation criteria may be applied. These criteria may be used alone or in combination.

A first example of such criteria is acceptable change in ambient pressure. If ambient pressure has changed by less than a predetermined value in a predetermined period of time (e.g., <1 mmHg in the past 5 minutes), the ventricular pressure measurement may be found reliable.

A second example of such criteria is valid telemetry link. The telemetry link between the external transceiver 35 and the internal telemetry unit 25 may be deemed reliable through positive verification of the link performance via error detection schemes such as cyclic redundancy checks or other means known in the art.

A third example of such criteria is recent recalibration. The system may require physician recalibration of the in vivo pressure sensor on a regular basis using recalibration methods previously described. The system may contain a reminder. If the device has not been recalibrated within the specified time, the pressure measurements would be deemed to be unreliable.

A fourth example of such criteria is valid pressure signal. The pressure signal may be evaluated to determine that the PTC is patent at the time that pressure measurements are obtained. This could be done by assessing variability of the pressure signal over a fixed time period. This assessment may be performed by evaluating variability in one or more parameters derived from the signal, such as max dP/dt, systolic pressure, diastolic pressure or mean pressure. One approach is to establish a measure of variability, such as parameter variance, standard error, etc., at the time of implantation. Occasional evaluation of variability may be performed automatically or upon activation by a physician during an office visit, for example. The assessment could be done by the computer 45 or the VAD controller 20.

Another approach to dealing with a potentially unreliable pressure signal is to use pressure as the primary feedback parameter and use the motor current as a back-up feedback when the pressure signal is found unreliable using criteria described above. The reliability of the pressure signal may be performed in real time, and if the pressure signal is deemed unreliable, the VAD control circuit reverts to motor current feedback, or another feedback means (e.g., flow measurement).

From the foregoing, it will be apparent to those skilled in the art that the present invention provides, in exemplary no-limiting embodiments, a variety of devices, systems and methods for providing effective, long term and reliable use of pressure feedback in VADs. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of calibrating a pressure sensor that measures left ventricular pressure and is associated with a ventricular assist device (VAD) implanted in a patient, comprising:
    observing, using a non-invasive imaging technique, a ventricular geometry of the patient for an indication of ventricular collapse or onset of ventricular collapse of the patient's left ventricle;
    gradually increasing flow rate of the VAD until an initial indication of ventricular collapse is observed; and
    calibrating the pressure sensor that measures left ventricular pressure based upon the initial indication of ventricular collapse.

2. A method of calibrating a pressure sensor that measures left ventricular pressure as in claim 1, wherein observing the ventricular geometry of the patient comprises a non-surgical diagnostic technique.

3. A method of calibrating a pressure sensor that measures left ventricular pressure as in claim 1, wherein the non-invasive imaging technique comprises ultrasonic imaging.

4. A method of calibrating a pressure sensor that measures left ventricular pressure as in claim 1, wherein the pressure sensor provides a pressure feedback signal to the VAD for use in controlling a motor speed of the VAD.

5. A method of calibrating a pressure sensor that measures left ventricular pressure as in claim 1, wherein the pressure sensor is disposed on a left ventricle free wall.

* * * * *